(12) United States Patent
Patibandla et al.

(10) Patent No.: US 11,959,917 B2
(45) Date of Patent: Apr. 16, 2024

(54) METHODS AND REAGENTS FOR ZIKA VIRUS IMMUNOASSAYS

(71) Applicant: Siemens Healthcare Diagnostics Inc., Tarrytown, NY (US)

(72) Inventors: Sai Patibandla, Baldwin Place, NY (US); Krishna Singh, New York, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/250,857

(22) PCT Filed: Sep. 18, 2019

(86) PCT No.: PCT/US2019/051630
§ 371 (c)(1),
(2) Date: Mar. 12, 2021

(87) PCT Pub. No.: WO2020/061135
PCT Pub. Date: Mar. 26, 2020

(65) Prior Publication Data
US 2022/0034882 A1 Feb. 3, 2022

Related U.S. Application Data

(60) Provisional application No. 62/732,964, filed on Sep. 18, 2018.

(51) Int. Cl.
*G01N 33/569* (2006.01)
(52) U.S. Cl.
CPC ... *G01N 33/56983* (2013.01); *G01N 2333/18* (2013.01); *G01N 2469/20* (2013.01)

(58) Field of Classification Search
None
See application file for complete search history.

(56) References Cited

U.S. PATENT DOCUMENTS

| 5,863,720 A | 1/1999 | Tedder |
| 6,391,540 B1 | 5/2002 | Chien et al. |
| 2017/0059566 A1* | 3/2017 | Reed ................ G01N 33/54389 |

(Continued)

FOREIGN PATENT DOCUMENTS

| AU | 6007694 | 8/1994 |
| CN | 1263599 | 8/2000 |

(Continued)

OTHER PUBLICATIONS

White, Stephen: brochure by abeam, Discover More, "ab213327 anti-Zika virus IgM (mu) capture ELISA kit"; Version 2. Jun. 14, 2016.

(Continued)

*Primary Examiner* — Michelle S Horning (57) ABSTRACT

Disclosed herein are immunoassay methods and reagents for detecting anti-Zika IgM antibody in a biological sample from a subject and/or diagnosing Zika virus infection in a subject. Also disclosed are algorithms for implementing the disclosed methods. The disclosed immunoassay methods, reagents, and algorithms enable efficient and reliable qualitative detection of anti-Zika virus antibodies and rapid determination of presumptive positive results for Zika virus infection in human subjects.

33 Claims, 1 Drawing Sheet

(56) References Cited

U.S. PATENT DOCUMENTS

| | | | |
|---|---|---|---|
| 2018/0136225 A1 | 5/2018 | Wong et al. | |
| 2018/0238881 A1 | 8/2018 | Lu et al. | |
| 2018/0292394 A1* | 10/2018 | Soldo | B01D 15/3809 |

FOREIGN PATENT DOCUMENTS

| | | |
|---|---|---|
| CN | 106518990 | 3/2017 |
| CN | 106841601 | 6/2017 |
| CN | 108291912 | 7/2018 |
| CN | 108445210 | 8/2018 |
| EP | 1304574 | 4/2003 |
| JP | H01118769 | 5/1989 |
| JP | H7027764 A | 1/1995 |
| JP | H1-118769 A | 1/1999 |
| JP | 11-287801 A | 10/1999 |
| JP | 2001506749 A | 5/2001 |
| WO | 2017039967 | 3/2017 |
| WO | 2017174193 | 10/2017 |
| WO | 2017197477 | 11/2017 |
| WO | 2017200008 | 11/2017 |
| WO | 2017211713 | 12/2017 |
| WO | 2018026845 | 2/2018 |
| WO | 2018092969 | 5/2018 |
| WO | 2018102659 | 6/2018 |

OTHER PUBLICATIONS

Unknown: "ADVIA Centaur Zika test (Siemens Healthcare Diagnostic Inc.)—Letter of Authorization"; Sep. 18, 2017.
Balmaseda, Angel et al: "Comparsion of Four Serological Methods and Two Reverse Transcription-PRC Assays or Diagnostics and Surveillance of Zika Virus Infection"; Journal of Clinical Microbiology; vol. 56, No. 3, Jan. 5, 2018.
Siemens: "Zika Test"; Oct. 2017, pp. 1-24; [retrieved on Apr. 18, 2022], www.fda.gov/media/107531/download.
Siemens Healthcare Diagnostics Inc.: "Fact Sheet for Healthcare Providers Interpreting ADVIA Centaur Zika Test results"; Sep. 18, 2017, pp. 1-4 [retrieved on Apr. 18, 2022], www.fda.gov/media/107512/download.
International Search Report for PCT/US2019/051630 dated Dec. 4, 2019.
FDA Letter to Siemens Healthcare Diagnostics Inc. responsive to Section 510(k) premarket notification of intent to market, 510(k) No. K191578, Trade/Device Name: ADVIA Centaur Zika test, ADVIA Centaur Zika Ab (100 tests), ADVIA Centaur Zika IgM (50 tests), ADVIA Centaur Zika Ab Quality Control, ADVIA Centaur Zika IgM Quality Control, Dated: Jun. 12, 2019, Department of Health and Human Services Food and Drug Administration, Indications for Use, pp. 1-12.
"Revocation of Authorization of Emergency Use of an In Vitro Diagnostic Device for Detection and/or Diagnosis of Zika Virus", Docket No. FDA-2019-N-3277, Federal Register, vol. 84, No. 179, Sep. 16, 2019, Notices, pp. 48625-48628.
Zika: The basics of the virus and how to protect against it. CDC's response to Zika. Centers for Disease Control and Prevention website. www_cdc_gov/zika/pdfs/fs-zika-basics_pdf. Published Jun. 27, 2017. Accessed: Aug. 12, 2016.
Petersen L R, Jamieson D J, Powers A M, Honein A M, Zika virus. N Engl J Med. 2016; 374 (16): 1552-1563.
Rabe I B, Staples J E, Villanueva J, et al. Interim guidance for Interpretation of Zika virus antibody test results. MMWR. 2016; 65(21):543-546.
Musso D, Gubler D J. Zika virus. Clin Microbiol Rev. Jul. 2016; 29(3):487-524.

* cited by examiner

METHODS AND REAGENTS FOR ZIKA VIRUS IMMUNOASSAYS

TECHNICAL FIELD

Disclosed herein are methods of detecting an anti-Zika virus IgM antibody in a biological sample from a human subject and methods of diagnosing Zika virus infection in the subject.

BACKGROUND

Zika virus is a single-stranded, positive-sense RNA virus (Musso D, Gubler D J. Zika virus. Clin Microbiol Rev. 2016 July; 29(3):487-524) belonging to the family Flaviviridae which includes closely related dengue, West Nile, Japanese encephalitis, and yellow fever viruses (Rabe I B, Staples J E, Villanueva J, et al. Interim guidance for Interpretation of Zika virus antibody test results. MMWR. 2016; 65(21):543-546). Zika virus was first isolated from rhesus monkey in the Zika forest of Uganda in 1947 (Musso et al., 2016). Zika virus infection was first reported in humans in Nigeria in 1954, and the first epidemic was reported on the Western Pacific Island of Yap in 2007 and later in French Polynesia in 2013 and 2014. Zika virus outbreak first emerged in the Americas in Brazil in March 2015, and spread to several countries and territories by March 2016 (Petersen L R, Jamieson D J, Powers A M, Honein A M, Zika virus. N Engl J Med. 2016; 374 (16): 1552-1563).

Zika virus infection is mainly transmitted by bite of an infected mosquito (*Aedes aegypti*). However, transmission from mother to fetus during pregnancy and through sexual contact with infected partners has been reported (id.). Potential transmission through blood transfusion has been documented (Musso et al., 2016). Most people infected with Zika virus exhibit mild symptoms or are asymptomatic (do not develop symptoms) (Zika: The basics of the virus and how to protect against it. CDC's response to Zika. Centers for Disease Control and Prevention website www cdc gov7zika/pdfs/fs-zika-basicspdf. Published Jun. 27, 2017. Accessed: Aug. 12, 2016). Common symptoms include fever, rash, joint pain and red eyes and these symptoms can be observed for up to a week (Petersen et al., 2016). Zika virus infection in pregnant women may cause microcephaly in the fetus, a major public health concern. The association of Zika virus infection with Guillain-Barre syndrome, a neurological illness that can cause temporary paralysis, has also been reported (Musso et al., 2016; Petersen et al., 2016).

During Zika virus infection, viremia is expected for one week after onset of symptoms, and Zika virus-specific IgM antibodies are reported to develop during the first week after development of symptoms and are expected to persist up to 12 weeks (Rabe et al, 2016). The detection of Zika virus-specific IgM antibodies is used for diagnosis and appropriate clinical management of the suspected Zika virus infected patient (id.).

The emergence of Zika virus infection outbreak in the Americas in 2015-2016 required urgent development of a diagnostic test to detect Zika-virus specific IgM antibodies in individuals recently infected with Zika virus for their appropriate clinical management.

Immunoassays have been developed for the detection of anti-Zika IgM antibodies in biological samples from human subjects, but available immunoassays suffer from various deficiencies including: 1) non-specific reactivity with serum/plasma from normal donors and pregnant women, causing poor specificity in the Zika non-endemic population; 2) cross-reactivity to Zika IgG antibodies in the sample from the human subject, resulting in poor specificity in the Zika endemic population; 3) the need to test single samples with up to 3 different antigens in the same assay, increasing the time and cost to produce a result; and/or 4) the need to test each sample with at least two different assays, also increasing time and cost to produce a result. Therefore, a need persists for immunoassay methods and reagents for reliably and efficiently detecting anti-Zika virus IgM antibody in a biological sample from a subject.

SUMMARY

Disclosed herein are methods of detecting an anti-Zika virus IgM antibody in a biological sample from a human subject, the methods comprising a first immunoassay and, optionally, a second immunoassay, wherein the first immunoassay comprises: a) incubating the biological sample with an anti-human IgG Fc antibody, a labeled Zika virus antigen, and a solid support comprising an anti-human IgM antibody, wherein, in the presence of an anti-Zika virus IgG antibody, an anti-Zika virus IgM antibody, or an anti-Zika virus IgG antibody and an anti-Zika virus IgM antibody in the biological sample, a complex I is formed, the complex I comprising (i) the anti-Zika virus IgG antibody, the anti-Zika virus IgM antibody, or the anti-Zika virus IgG antibody and the anti-Zika virus IgM antibody, (ii) the labeled Zika virus antigen, and (iii) the solid support comprising the anti-human IgM antibody; and b) detecting the complex I, the presence of which indicates the presence of the anti-Zika virus IgM antibody, the anti-Zika virus IgG antibody, or the anti-Zika virus IgG antibody and the anti-Zika virus IgM antibody in the biological sample, and if the complex I is detected, performing the second immunoassay, comprising: c) incubating the biological sample with a solid support comprising an anti-human IgM antibody, and a labeled Zika virus antigen, wherein, in the presence of an anti-Zika virus IgM antibody in the biological sample, a complex II is formed, the complex II comprising (i) the solid support comprising the anti-human IgM antibody, (ii) the anti-Zika virus IgM antibody, and (iii) the labeled Zika virus antigen; and d) detecting the complex II, the presence of which indicates the presence of the anti-Zika virus IgM antibody in the biological sample.

Also disclosed are methods of detecting antibodies to Zika virus in a subject, the methods comprising performing a first immunoassay comprising:
  a) incubating a biological sample from the subject with:
    a solid support comprising an anti-human IgM antibody,
    an anti-human IgG Fc antibody, and
    a labeled Zika virus antigen,
    wherein, in the presence of an anti-Zika virus IgG antibody, an anti-Zika virus IgM antibody, or an anti-Zika virus IgG antibody and an anti-Zika virus IgM antibody in the biological sample, a complex I is formed, the complex I comprising (i) the solid support comprising the anti-human IgM antibody, (ii) the anti-Zika virus IgG antibody, the anti-Zika virus IgM antibody, or the anti-Zika virus IgG antibody and the anti-Zika virus IgM antibody, and (iii) the labeled Zika virus antigen;
  b) detecting the complex I, and
    $b_i$) if the complex I is not detected, determining that the subject is negative for antibodies to Zika virus; or
    $b_{ii}$) if the complex I is detected, determining that the subject is positive for anti-Zika virus antibodies.

The disclosed methods can further comprise performing a second immunoassay comprising:
c) incubating the biological sample with:
a solid support comprising an anti-human IgM antibody, and
a labeled Zika virus antigen,
wherein, in the presence of an anti-Zika virus IgM antibody in the biological sample, a complex II is formed, the complex II comprising (i) the solid support comprising the anti-human IgM antibody, (ii) the anti-Zika virus IgM antibody, and (iii) the labeled Zika virus antigen;
d) detecting the complex II, and
$d_i$) if the complex II is not detected, determining that the human subject is negative for anti-Zika virus IgM antibodies.

The disclosed methods can further comprise:
$d_{ii}$) if the complex II is detected, repeating steps c) and d) at least in duplicate, and
e) if the complex II is detected in the equivalent of at least 2 of 3 replicates, determining that the human subject is positive for anti-Zika virus IgM antibodies.

Also disclosed are kits comprising: a solid support, an anti-human IgM antibody, an anti-human IgG Fc antibody, and a labeled Zika virus antigen. The kits can comprise reagents for a first immunoassay and reagents for a second immunoassay, wherein the reagents for the first immunoassay comprise: a solid support, an anti-human IgM antibody, an anti-human IgG Fc antibody, and a labeled Zika virus antigen; and wherein the reagents for the second immunoassay comprise: a solid support, an anti-human IgM antibody, and a labeled Zika virus antigen. The kits can further comprise instructions for performing the first and the second immunoassays, wherein the instructions direct a user to perform the first immunoassay to determine the presence or absence of anti-Zika virus antibodies in a biological sample from a human subject, and wherein the instructions further direct the user to perform the second immunoassay only if it is determined in the first immunoassay that the biological sample is positive for anti-Zika virus antibodies.

Also disclosed herein are algorithms for performing the disclosed methods and methods of diagnosing Zika virus infection in a subject using the disclosed methods and algorithms.

BRIEF DESCRIPTION OF THE DRAWINGS

The summary, as well as the following detailed description, is further understood when read in conjunction with the appended drawings. For the purpose of illustrating the disclosed methods and kits, there are shown in the drawings exemplary embodiments of the methods and kits; however, the methods and kits are not limited to the specific embodiments disclosed. In the drawings.

DETAILED DESCRIPTION OF ILLUSTRATIVE EMBODIMENTS

The disclosed methods and kits may be understood more readily by reference to the following detailed description taken in connection with the accompanying figures, which form a part of this disclosure. It is to be understood that the disclosed methods and kits are not limited to the specific methods and kits described and/or shown herein, and that the terminology used herein is for the purpose of describing particular embodiments by way of example only and is not intended to be limiting of the claimed methods and kits.

Unless specifically stated otherwise, any description as to a possible mechanism or mode of action or reason for improvement is meant to be illustrative only, and the disclosed methods and kits are not to be constrained by the correctness or incorrectness of any such suggested mechanism or mode of action or reason for improvement.

Throughout this text, the descriptions refer to methods of detecting an antibody and methods of diagnosing Zika virus infection. Where the disclosure describes or claims a feature or embodiment associated with a method of detecting an antibody, such a feature or embodiment is equally applicable to the methods of diagnosing Zika virus infection. Likewise, where the disclosure describes or claims a feature or embodiment associated with a method of diagnosing Zika virus infection, such a feature or embodiment is equally applicable to the methods of detecting an antibody.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges were explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed methods and kits which are, for clarity, described herein in the context of separate embodiments, may also be provided in combination in a single embodiment. Conversely, various features of the disclosed methods and kits that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of."

Disclosed herein are immunoassays and methods for detecting anti-Zika virus IgM antibody in a biological sample from a human subject and/or diagnosing Zika virus infection in a human subject.

The methods disclosed herein can comprise incubating the biological sample with an anti-human IgG Fc antibody, a labeled Zika virus antigen, and a solid support comprising an anti-human IgM antibody. In the presence of an anti-Zika virus IgG antibody, an anti-Zika virus IgM antibody, or an anti-Zika virus IgG antibody and an anti-Zika virus IgM antibody in the biological sample, a complex I is formed, the complex I comprising (i) the anti-Zika virus IgG antibody, the anti-Zika virus IgM antibody, or the anti-Zika virus IgG antibody and the anti-Zika virus IgM antibody, (ii) the labeled Zika virus antigen, and (iii) the solid support comprising the anti-human IgM antibody. The method can further comprise detecting the complex I, the presence of which indicates the presence of the anti-Zika virus IgM antibody, the anti-Zika virus IgG antibody, or the anti-Zika virus IgG antibody and the anti-Zika virus IgM antibody in the biological sample. If the complex I is detected, the method can further comprise performing the second immunoassay, comprising incubating the biological sample with a solid support comprising an anti-human IgM antibody, and a labeled Zika virus antigen. In the presence of an anti-Zika virus IgM antibody in the biological sample, a complex II is formed, the complex II comprising (i) the solid support comprising the anti-human IgM antibody, (ii) the anti-Zika virus IgM antibody, and (iii) the labeled Zika virus antigen. The method can further comprise detecting the complex II, the presence of which indicates the presence of the anti-Zika virus IgM antibody in the biological sample.

In some embodiments, the Zika virus antigen is Zika virus NS1 antigen, or an immunogenic fragment thereof. The Zika virus NS1 antigen or immunogenic fragment thereof can be recombinant.

In some embodiments, the anti-human IgG Fc antibody can immunospecifically bind to an Fc region of a human IgG antibody. For example, the anti-human IgG Fc antibody can be a monoclonal or a polyclonal antibody raised against a human IgG Fc antigen. In some embodiments, the anti-human IgG Fc antibody is a goat-anti-human IgG Fc antibody. That is, the anti-human IgG Fc antibody can be a goat antibody to human IgG Fc.

Without wishing to be bound by theory, it is predicted that the anti-human IgG Fc antibody can bind to or otherwise couple with the solid support in the incubation reaction. For example, the anti-human IgG Fc can non-covalently bind to the solid support. Accordingly, in some embodiments, the anti-human IgG Fc antibody is indirectly linked to the solid support. In some embodiments, the anti-human IgG Fc antibody is a component of complex I.

The anti-human IgM antibody can be directly or indirectly linked to the solid support. In some embodiments, the anti-human IgM antibody is biotinylated and the solid support comprises streptavidin. Thus, the anti-human IgM antibody can be indirectly linked to the solid support through a biotin-streptavidin interaction. In some embodiments, the anti-human IgG Fc antibody is indirectly linked to the solid support. Additionally, the anti-human IgG Fc antibody can be biotinylated and thereby also indirectly linked to the solid support comprising streptavidin.

The biological sample can be serum or plasma, and it can further comprise an anticoagulant, including, for example, EDTA or heparin. In some embodiments, the biological sample is from a human. The biological sample is obtained from a human subject at least 8 days after onset of symptoms of Zika virus infection or risk of exposure to Zika virus. In some embodiments, the biological sample must be obtained from a human subject at least 8 days after onset of symptoms of Zika virus infection or risk of exposure to Zika virus to ensure accurate detection of anti-Zika virus IgM antibodies in the biological sample.

In the first immunoassay, the "Zika Ab" assay, the anti-human IgM antibody and the solid support can be present in a buffer comprising tricine, sodium chloride, TWEEN®20 (polyoxyethylene (20) sorbitan monolaurate) detergent, disodium EDTA, preservative, sulfhydryl-modified bovine serum albumin, and the anti-human IgG Fc antibody. In the second immunoassay, the "Zika M" assay, the IgM antibody and the solid support can be present in a buffer comprising tricine, sodium chloride, TWEEN®20 detergent, disodium EDTA, preservative, sulfhydryl-modified bovine serum albumin, but without the anti-human IgG Fc antibody.

The methods disclosed herein can further comprise determining a level of the anti-Zika virus IgG antibody, the anti-Zika virus IgM antibody, or the anti-Zika virus IgG antibody and the anti-Zika virus IgM antibody in the biological sample. In some embodiments, the level of the anti-Zika virus IgG antibody, the anti-Zika virus IgM antibody, or the anti-Zika virus IgG antibody and the anti-Zika virus IgM antibody in the biological sample is directly proportional to the level of the complex I or complex II detected. Detecting the signal, as used herein, can comprise measuring a signal from the label and comparing the signal to a control signal from a biological sample from a human known to be negative for anti-Zika virus antibodies.

In the event that the complex II is detected in the Zika M assay, the method can further include repeating the steps of the Zika M assay at least in duplicate and determining that the human subject is positive for anti-Zika virus IgM antibodies if the complex II is detected in the equivalent of at least 2 of 3 replicates.

Also disclosed herein are methods of diagnosing Zika virus infection in a subject comprising the disclosed methods of detecting anti-Zika virus IgM antibodies in a biological sample from a subject.

Figure 1:
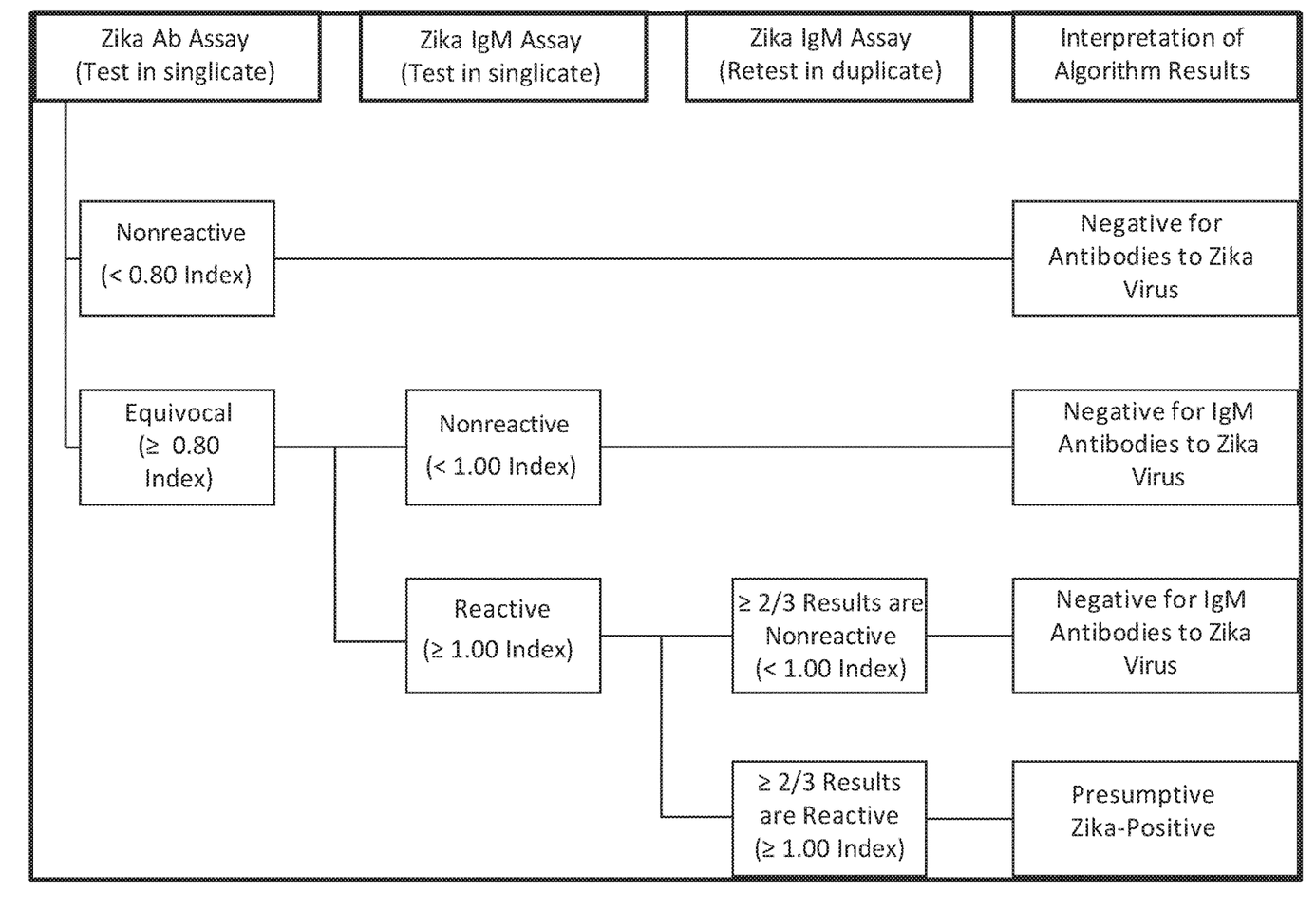
FIG. 1 is a schematic representation of an embodiment of the "Zika Test" algorithm, whereby a result of Negative for Antibodies to Zika Virus or Presumptive Zika-Positive is determined for a given biological sample from a subject.

Further disclosed are algorithms for detecting Zika virus-specific IgM antibodies in a biological sample (FIG. 1). The algorithms disclosed herein can guide a user or an automated system through the steps of detecting antibodies to Zika virus in a subject in a manner that increases efficiency and reliability of the methods disclosed herein. For example, the algorithms can be used to reduce the number of assays required for a particular sample to determine that it is, for example, negative for anti-Zika virus IgM antibodies. In some embodiments, the algorithms comprise a set of instructions to guide a user or an automated system through the methods of detecting antibodies to Zika virus in a biological sample. An example algorithm can instruct the user or system to perform a method of detecting antibodies to Zika virus in a subject comprising performing a first immunoassay comprising:

a) incubating a biological sample from the subject with:
  a solid support comprising an anti-human IgM antibody,
  an anti-human IgG Fc antibody, and
  a labeled Zika virus antigen,
  wherein, in the presence of an anti-Zika virus IgG antibody, an anti-Zika virus IgM antibody, or an anti-Zika virus IgG antibody and an anti-Zika virus IgM antibody in the biological sample, a complex I is formed, the complex I comprising (i) the solid support comprising the anti-human IgM antibody, (ii) the anti-Zika virus IgG antibody, the anti-Zika virus IgM antibody, or the anti-Zika virus IgG antibody and the anti-Zika virus IgM antibody, and (iii) the labeled Zika virus antigen;
b) detecting the complex I, and
b$_i$) if the complex I is not detected, determining that the subject is negative for antibodies to Zika virus; or
b$_{ii}$) if the complex I is detected, determining that the subject is positive for anti-Zika virus antibodies.

The algorithms can further instruct the user or the system to terminate the assays if the complex I is not detected in step b$_i$, thereby reducing the number of assays, the amount of reagents, and the time required to detect anti-Zika virus antibodies in a biological sample. However, if in step b) a result is obtained that is equivocal (i.e., "reactive"), then the algorithm can instruct the user or system to perform a second immunoassay comprising:

c) incubating the biological sample with:
a solid support comprising an anti-human IgM antibody, and
a labeled Zika virus antigen,
wherein, in the presence of an anti-Zika virus IgM antibody in the biological sample, a complex II is formed, the complex II comprising (i) the solid support comprising the anti-human IgM antibody, (ii) the anti-Zika virus IgM antibody, and (iii) the labeled Zika virus antigen;
d) detecting the complex II, and
d$_i$) if the complex II is not detected, determining that the human subject is negative for anti-Zika virus IgM antibodies.

The algorithm can instruct the user or system to terminate the assays if the complex II is not detected in step d). Otherwise, the algorithm can proceed through the additional method steps comprising:
d$_{ii}$) if the complex II is detected, repeating steps c) and d) at least in duplicate, and
e) if the complex II is detected in the equivalent of at least 2 of 3 replicates, determining that the human subject is positive for anti-Zika virus IgM antibodies.

In some embodiments of the methods and algorithms for implementing the methods disclosed herein, a biological sample known to have, or suspected of having, anti-Zika virus antibodies is incubated with a labeled Zika virus antigen and solid support having an anti-human IgM antibody bound thereto. In the absence of the anti-Zika virus antibodies, the labeled Zika virus antigen will not bind to or otherwise interact with the solid support. Thus, in the absence of the anti-Zika virus antibodies in the biological sample, the labeled Zika virus antigen remains in the solution and isolation of the solid support does not result in isolation of the labeled antigen. When the anti-Zika virus antibodies are present in the biological sample, on the other hand, the anti-Zika virus antibodies simultaneously bind to the anti-human IgM antibody bound to the solid support and the labeled Zika virus antigen, thereby linking the labeled antigen and the solid support and resulting in the formation of a solid support/labeled antigen complex. It is to be understood that the order in which the incubation takes place can be different from that described herein. Furthermore, the labeled and solid-support-bound reaction components can be rearranged in alternative embodiments of the presently described immunoassays. For example, the biological sample known to have, or suspected of having, anti-Zika virus antibodies can be incubated with a solid support having an unlabeled Zika virus antigen bound thereto followed by incubation with a labeled anti-human IgM antibody. In other embodiments, the biological sample known to have, or suspected of having, anti-Zika virus antibodies can be simultaneously incubated with a solid support having, on the one hand, an unlabeled anti-human IgM antibody bound thereto and a labeled Zika virus antigen, or, on the other hand, an unlabeled Zika virus antigen bound thereto and an anti-human IgM antibody.

The biological sample known to have, or suspected of having, anti-Zika virus antibody can be incubated in a reaction mixture for a period of time sufficient to achieve a partial reaction without allowing the reaction to achieve equilibrium, such as for about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes about 18 minutes, about 19 minutes, or less than about 20 minutes. The labeled Zika virus antigen can be added and incubated with the biological sample for about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes about 18 minutes, about 19 minutes, or less than about 20 minutes. The solid support having anti-human IgM antibody bound thereto can be added to the mixture of biological sample and labeled Zika virus antigen and incubated for a period of time sufficient to achieve a partial reaction without allowing the reaction to achieve equilibrium, such as for about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes about 18 minutes, about 19 minutes, or less than about 20 minutes. In some embodiments, the incubating steps are performed in a total of about 10 minutes to about 20 minutes, about 20 minutes to about 30 minutes, about 30 minutes to about 40 minutes, about 40 minutes to about 50 minutes, or about 50 minutes to about an hour. The subsequent detecting can be performed in less than about 5 minutes, less than about 10 minutes, less than about 15 minutes, or less than about 20 minutes. It is to be understood that the amount of time needed for the assays or any step or steps thereof may vary based upon several factors including the level of the anti-Zika virus antibodies in the biological sample and the affinity of the anti-human IgM antibody for the anti-Zika virus antibodies in the biological sample. In some embodiments, incubating the biological sample with the reaction mixture can be performed for a period of time sufficient to enable the reaction to achieve equilibrium, such as on the order of 1 or more hours. Thus, the disclosed methods can be performed for any suitable amount of time.

The anti-human IgM antibody can be directly or indirectly linked to the solid support. Suitable techniques for directly linking the anti-human IgM antibody to the solid support include, for example, covalent attachment, adsorption, non-covalent interaction, or combinations thereof. In some embodiments, the anti-human IgM antibody can be directly linked to the solid support by N-hydroxysuccinimide (NHS) chemistry or by 1-Ethyl-3-(3-dimethylaminopropyl)carbodiimide (EDC) NHS chemistry. Suitable techniques for indirectly linking the anti-human IgM antibody to the solid support include, for example, linking through a peptide, a protein, an antibody, a linker, or a combination thereof. In some embodiments, the anti-human IgM antibody can be indirectly linked to the solid support through streptavidin and biotin. For example, the anti-human IgM antibody can be biotinylated and the solid support can comprise streptavidin. It is to be understood that the same chemistry can be applied to any reaction component linked to the solid support in alternative embodiments of the disclosed immunoassays.

Exemplary solid supports include, but are not limited to, a column matrix material, a culture plate, a tube, a dish, a flask, a microtiter plate, a bead/particle, heat-killed formalin-(or other chemically)-fixed prokaryotic or eukaryotic cells, microscope slides, ACLAR® Film, or any other optically transparent polymer, or a combination thereof. The solid support can be fully or partially composed of plastic, cellulose, cellulose derivatives, nitrocellulose, glass, fiberglass, latex, or a combination thereof. In some embodiments, the solid support comprises a magnetic bead/particle. In some embodiments, the magnetic bead/particle is a paramagnetic particle (PMP). In some embodiments, the magnetic bead/particle is a latex magnetic particle (LMP).

The label can be any suitable label known to those skilled in the art to be useful for creating a detectable signal. Suitable detectable labels include, but are not limited to, enzyme conjugates (e.g., horseradish peroxidase (HRP), alkaline phosphatase, glucose oxidase, and β-galactosidase), fluorescent probes, radioactive isotopes, chemiluminescent compounds, bioluminescent compounds, or combination thereof. In some embodiments, the label is an acridinium ester ("AE") or an analog thereof. Suitable AE analogs include: dimethyl acridinium ester (DMAE), N-sulfopropyl dimethyl acridinium ester (NSP-DMAE), high quantum yield acridinium ester (HQYAE, acridinium, 9-[[4-[[[6-[(2,5-dioxo-1-pyrrolidinyl)oxy]-6-oxohexyl]amino]carbonyl]-2,6-dimethylphenoxy]carbonyl]-2,7-bis(3,6,9,12,15,18-hexaoxanonadec-1-yloxy)-10-(3-sulfopropyl)-, inner salt), Zwitterionic acridinium ester (ZAE, Acridinium, 9-[[4-[[[3-[[3-[[5-[(2,5-dioxo-1-pyrrolidinyl)oxy]-1,5-dioxopentyl]amino]propyl]methyl(3-sulfopropyl)ammonio]propyl]amino]carbonyl]-2,6-dimethylphenoxy]carbonyl]-10-(3-sulfopropyl)-, bis(inner salt)), N-sulfopropyl-2-isopropoxy dimethyl acridinium ester (Iso-Di-ZAE), trisulfopropyl acridinium ester (TSP-AE), or N-sulfopropyl dimethyl acridinium ester with hexa(ethylene)glycol linker (HEG-GLU-AE). In some embodiments, the labeled Zika virus antigen comprises Zika NS1:NSP-DMAE-NHS.

The anti-human IgM antibody can be an IgA, IgD, IgG, IgE, or IgM isotype or a single domain format, such as a single-domain antibody from camelid. In some embodiments, the anti-human IgM antibody is an IgG isotype. In some embodiments, the anti-human IgM antibody is a commercially available anti-human IgM antibody. Aptamers that are specific for the human IgM antibodies can also be used.

In some embodiments, the immunoassays disclosed herein meet one or more of the following clinical requirements:
a. ≥90% positive and negative agreement;
b. Repeatability 0.80-2.00 Index: ≤12.0% and >2.00 Index: ≤8.0%;
c. Within-Run Precision 0.80-2.00 Index: ≤15.0% and >2.00 Index: ≤10.0%;
d. Calibration Interval ≥7 Days;
e. On-Board Stability ≥14 Days;
f. Control System that is capable of maintaining consistent standardization & performance.
g. Interference and Reproducibility In some embodiments, the immunoassays disclosed herein meet all of the above clinical requirements a.-f.

In some embodiments, the disclosed immunoassays are intended for in vitro diagnostic use in the presumptive qualitative detection of IgM antibodies to the Zika virus in serum and plasma (potassium EDTA or lithium heparin, each collected alongside a patient-matched serum specimen) specimens collected from individuals meeting Centers for Disease Control and Prevention (CDC) Zika virus clinical criteria (e.g. a history of clinical signs and symptoms associated with Zika virus infection) and/or CDC Zika virus epidemiological criteria (for instance, history of residence in or travel to a geographic region with active Zika transmission at the time of travel, or other epidemiological criteria for which Zika virus testing may be indicated). In some embodiments, specimens from symptomatic patients or returning travelers from endemic areas are not collected prior to 8 days after onset of symptoms or risk of exposure, respectively.

In some embodiments of the disclosed immunoassays, the first immunoassay, the "Zika Ab" assay, and the optional second immunoassay, the "Zika M" assay can be in 2-pass immunoassay format. The Zika Ab assay can be an antibody capture immunoassay using a 2-pass format. In the first pass, patient sample can be incubated in a cuvette, for example, with anti-human IgM antibody linked to a solid support. During incubation, solid-support-bound anti-human IgM antibody binds to antibodies from the patient sample. The captured antibodies can be washed and resuspended. In the second pass, the patient anti-Zika virus antibodies captured on the solid support can be incubated with Zika virus NS1 antigen labeled with any suitable chemiluminescent or other labeling reagent. The labeled NS1 antigen binds to patient Zika virus antibodies on the solid support during incubation. The NS1/solid support complex can be washed and subjected to, e.g., chemiluminescent detection.

The Zika M assay can be an IgM capture immunoassay using a 2-pass format. In the first pass the solid support, coated with anti-human IgM antibody and patient sample can be incubated in the cuvette for binding anti-Zika virus IgM antibodies from the patient sample to the solid support. The captured anti-Zika virus IgM antibodies can be washed and resuspended. In the second pass, the anti-Zika virus IgM antibodies captured on the solid support can be incubated with labeled NS1 for binding of the NS1 antigen to the captured anti-Zika virus IgM antibodies on immobilized on the solid support. The NS1/solid support complex can be washed and subjected to, e.g., chemiluminescent detection.

The disclosed methods can be performed manually or can be automated. For example, the disclosed methods can be performed using an ADVIA CENTAUR® Immunoassay System or an ATELLICA™ system. For example, a system can be automated to perform the following actions for both Zika Ab and Zika M assays:
1. Dispense sample into a cuvette.
2. Dispense buffer containing solid support with anti-human IgM antibody bound thereto, and incubate for, e.g., 18.25 minutes at 37° C.
3. Separate/isolate solid support, aspirate, and wash the cuvette with wash reagent.
4. Dispense buffer containing chemiluminescent-labeled NS1 antigen and incubate, e.g., 18 minutes at 37° C.
5. Separate/isolate solid support, aspirate, and wash the cuvette with wash reagent.
6. Dispense chemiluminescence reagent to initiate the chemiluminescent reaction.
7. Report results according to a user-selected option.

In a particular embodiment, the disclosed immunoassays can be adapted for use on an ADVIA CENTAUR® Immunoassay System (Siemens Healthcare, AG), and/or an ADVIA CENTAUR® Immunoassay System can be automated to perform the above actions.

In some embodiments, a direct relationship exists between the level of anti-Zika virus antibodies (i.e., anti-Zika virus IgG antibodies or anti-Zika virus IgM antibodies) or anti-Zika virus IgM antibodies present in the patient sample and the amount of relative light units (RLUs) detected by the system.

In some embodiments, the immunoassays disclosed herein employ the following raw materials in the Zika Ab and/or Zika M assays:

Zika virus NS1 recombinant antigen: The disclosed immunoassays can use Zika virus NS1 recombinant antigen, for example, from Meridian Life Science. The Zika virus NS1 recombinant antigen can be expressed in insect cells and purified by affinity chromatography.

Anti-human IgM antibody: The anti-human IgM antibody can be a monoclonal antibody against human IgM. In some embodiments, it can be biotin-conjugated.

In some embodiments, it can be produced by labelling an anti-human IgM monoclonal antibody with NHS-LC-LC-Biotin.

SERA-MAG Magnetic Streptavidin Microparticles (MG-SA): The SERA-MAG Magnetic Streptavidin Microparticles (MG-SA) microparticles (GE HealthCare Bio-Sciences Corp.) can be used as a solid support to prepare a wetcake comprising the solid support coated with the anti-human IgM antibody.

Goat Antiserum to Human IgG, Fc Specific: The Goat Antiserum to Human IgG, Fc Specific ("goat-anti-human IgG, Fc"), for example from Nittobo or Meridian Life Sciences, can be employed in the Zika Ab assay.

In some embodiments, the immunoassays disclosed herein comprise the following example reagent formulations.

TABLE 1

Example Zika Ab Solid Support Buffer Formulation

| Component | Conc. | Function |
|---|---|---|
| Tricine | 18.0 g/L | Buffer Salt |
| Sodium Chloride | 15.0 g/L | Ionic Strength |
| Disodium EDTA | 0.7 g/L | Chelating Agent |
| MICROPROTECT ™ preservative | 2.50 mL/L | Preservative/Anti-microbial |
| TWEEN ® 20 detergent | 2.20 g/L | Detergent (Blocking Agent) |
| Sodium Azide | 0.9 g/L | Preservative/Anti-microbial |
| Heat Inactivated Goat Serum | 50.0 mL/L | Protein (Blocking Agent) |
| BSA, Sulfhydryl Modified | 10.0 g/L | Protein (Blocking Agent) |
| Goat Anti-Human IgG FC | 1.35 g/L | Protein (Blocking Agent) |
| Zika M/Zika Ab Wetcake | 0.1 g/L | Capture Human IgM Antibodies |
| pH = 8.0 | | |

TABLE 2

Example Zika Ab Ancillary Well Reagent Formulation

| Component | Conc. | Function |
|---|---|---|
| EPPS | 25.3 g/L | Buffer Salt |
| Sodium Chloride | 15.0 g/L | Ionic Strength |
| TWEEN ® 20 detergent | 2.20 g/L | Detergent (Blocking Agent) |
| Disodium EDTA | 0.70 g/L | Chelating Agent |
| MICROPROTECT ™ preservative | 1.0 mL/L | Preservative/Anti-microbial |

TABLE 2-continued

Example Zika Ab Ancillary Well Reagent Formulation

| Component | Conc. | Function |
|---|---|---|
| Sodium Azide | 0.9 g/L | Preservative/Anti-microbial |
| BSA, Sulfhydryl Modified | 10.0 g/L | Protein (Blocking Agent) |
| Heat Inactivated Goat Serum | 400 mL/L | Protein (Blocking Agent) |
| pH = 8.0 | | |

TABLE 3

Example Zika Ab Visualization Buffer Formulation

| Component | Conc. | Function |
|---|---|---|
| EPPS | 25.3 g/L | Buffer Salt |
| Sodium Chloride | 15.0 g/L | Ionic Strength |
| TWEEN ® 20 detergent | 2.20 g/L | Detergent (Blocking Agent) |
| Disodium EDTA | 0.70 g/L | Chelating Agent |
| MICROPROTECT ™ preservative | 1.0 mL/L | Preservative/Anti-microbial |
| Sodium Azide | 0.9 g/L | Preservative/Anti-microbial |
| BSA, Sulfhydryl Modified | 10.0 g/L | |
| Zika M/ZikaAb Visualization Buffer (Zika NS1: NSP-DMAE-NHS) | 0.40 mg/L | Zika Antibodies detection |
| pH = 8.0 | | |

TABLE 4

Example Zika M Solid Support Buffer Formulation

| Component | Conc. | Function |
|---|---|---|
| Tricine | 18.0 g/L | Buffer Salt |
| Sodium Chloride | 15.0 g/L | Ionic Strength |
| Disodium EDTA | 0.7 g/L | Chelating Agent |
| MICROPROTECT ™ preservative | 2.50 mL/L | Preservative/Anti-microbial |
| TWEEN ® 20 detergent | 2.20 g/L | Detergent (Blocking Agent) |
| Pluronic P-105 | 5.0 g/L | Detergent (Blocking Agent) |
| Sodium Azide | 0.9 g/L | Preservative/Anti-microbial |
| Heat Inactivated Goat Serum | 50.0 mL/L | Protein (Blocking Agent) |
| BSA, Sulfhydryl Modified | 10.0 g/L | Protein (Blocking Agent) |
| Zika M/Zika Ab Wetcake | 0.1 g/L | Capture Human IgM Antibodies |
| pH = 8.0 | | |

TABLE 5

Example Zika M Ancillary Well Reagent Formulation

| Component | Conc. | Function |
|---|---|---|
| EPPS | 25.3 g/L | Buffer Salt |
| Sodium Chloride | 15.0 g/L | Ionic Strength |
| TWEEN ® 20 detergent | 2.20 g/L | Detergent (Blocking Agent) |
| Pluronic P-105 | 5.0 g/L | Detergent (Blocking Agent) |
| Disodium EDTA | 0.70 g/L | Chelating Agent |
| MICROPROTECT ™ preservative | 1.0 mL/L | Preservative/Anti-microbial |
| Sodium Azide | 0.9 g/L | Preservative/Anti-microbial |
| BSA, Sulfhydryl Modified | 10.0 g/L | Protein (Blocking Agent) |
| Heat Inactivated Goat Serum | 400 mL/L | Protein (Blocking Agent) |
| pH = 8.0 | | |

TABLE 6

Example Zika M Visualization Buffer Formulation

| Component | Conc. | Function |
|---|---|---|
| EPPS | 25.3 g/L | Buffer Salt |
| Sodium Chloride | 15.0 g/L | Ionic Strength |
| TWEEN ® 20 detergent | 2.20 g/L | Detergent (Blocking Agent) |
| Pluronic P-105 | 5.0 g/L | Detergent (Blocking Agent) |
| Disodium EDTA | 0.70 g/L | Chelating Agent |
| MICROPROTECT ™ preservative | 1.0 mL/L | Preservative/Anti-microbial |
| Sodium Azide | 0.9 g/L | Preservative/Anti-microbial |
| BSA, Sulfhydryl Modified | 10.0 g/L | Protein (Blocking Agent) |
| Zika M/ZikaAb Visualization Buffer (Zika NS1: NSP-DMAE-NHS) | 0.40 mg/L | Zika Antibodies detection |
| pH = 8.0 | | |

TABLE 7

Example Zika M/Zika Ab Wetcake Formulation

| Component | Conc. | Function |
|---|---|---|
| Tricine | 18.0 g/L | Buffer Salt |
| Sodium Chloride | 15.0 g/L | Ionic Strength |
| Disodium EDTA | 0.7 g/L | Chelating Agent |
| MICROPROTECT ™ preservative | 2.50 mL/L | Preservative/Anti-microbial |
| TWEEN ® 20 detergent | 2.20 g/L | Detergent (Blocking Agent) |
| Sodium Azide | 0.9 g/L | Preservative/Anti-microbial |
| BSA, Sulfhydryl Modified | 10.0 g/L | Protein (Blocking Agent) |
| SERA-MAG Magnetic Streptavidin Microparticles (MG-SA) | 5 g/L | Solid support for analyte capture conjugate |
| Conj Biotin Ab huIgM | 0.04 mg/mg | Coat Biotin conjugate on MG-SA |
| pH = 8.0 | | |

Suitable biological samples for detecting the anti-Zika virus antibody include any biological sample from a subject that contains, or is suspected of containing, anti-Zika virus antibody including, but not limited to, serum or plasma.

The immunoassays disclosed herein employ a Zika virus antigen. In some embodiments, the Zika virus antigen is Zika virus NS1 antigen. In some embodiments, the Zika virus antigen is recombinant Zika virus NS1 antigen. The Zika virus antigen can be expressed in heterologous cells, for example, insect cells. In some embodiments, the Zika antigen further comprises an epitope tag. The epitope tag can be at the N-terminus or at the C-terminus of the Zika virus antigen. The epitope tag can be any suitable tag known to persons skilled in the art including, but not limited to, a 6-histidine tag, a hemagglutinin tag, a glutathione-S-transferase, a maltose binding protein, or a chitin binding protein. In some embodiments, the Zika virus antigen comprises a C-terminal 6-histidine tag.

Further disclosed herein are kits. The kits can comprise a solid support, an anti-human IgM antibody, an anti-human IgG Fc antibody, and a labeled Zika virus antigen. In some embodiments, the kits can comprise reagents for a first immunoassay and reagents for a second immunoassay, wherein the reagents for the first immunoassay comprise: a solid support, an anti-human IgM antibody, an anti-human IgG Fc antibody, and a labeled Zika virus antigen; and wherein the reagents for the second immunoassay comprise: a solid support, an anti-human IgM antibody, and a labeled Zika virus antigen. The kits can further comprise instructions for performing the first and the second immunoassays. The instructions can direct a user or system to perform the first immunoassay to determine the presence or absence of anti-Zika virus antibodies in a biological sample from a human subject. The instructions can further direct the user or system to perform the second immunoassay only if it is determined in the first immunoassay that the biological sample is positive for anti-Zika virus antibodies.

Suitable solid supports and labels for any of the kits disclosed herein include those solid supports and labels disclosed for the methods above.

EXAMPLES

The following examples are provided to further describe some of the embodiments disclosed herein. The examples are intended to illustrate, not to limit, the disclosed embodiments.

Development of a Highly Specific and Efficient Anti-Zika IgM Antibody Immunoassay A "Zika Ab" assay with anti-human IgG Fc antibodies present in the reaction buffer was prepared alongside another "Zika M" assay without anti-human IgG Fc antibodies. Using both Zika Ab and Zika M assays, a Zika Test algorithm was developed (FIG. 1). Per the Zika Test algorithm, each biological sample is tested first by the Zika Ab assay (including the anti-human IgG Fc antibodies) and only reactive samples in which either anti-Zika IgM or anti-Zika IgG or anti-Zika IgM and anti-Zika IgG antibodies are detected are to be subsequently tested with the Zika M assay.

Because the Zika Ab assay provides high specificity in the non-endemic population and can detect both Zika-specific IgG and IgM antibodies, this assay identifies biological samples (i.e., individuals) containing Zika-specific antibodies. Subsequent testing of these samples with the Zika M assay without anti-human IgG Fc antibodies, which detects only Zika-specific IgM antibodies, identifies those samples (i.e., individuals) with anti-Zika IgM antibodies. These individuals are presumed recently infected with Zika virus.

Because the Zika Test algorithm requires testing by the Zika Ab assay one time only, and a majority of the tested population are expected to be negative for Zika infection, a majority of samples will be tested with the Zika Ab assay only. Therefore, the Zika Test algorithm provides a simple solution to achieve high specificity and sensitivity in assaying for recent Zika infection in an individual.

Materials

A reagent formulation was finalized for the Zika Ab immunoassay (Table 8) and for the Zika M assay (Table 9).

TABLE 8

Zika Ab assay formulation with goat-anti-human IgG Fc

| Buffer (pH 8.0) | | Ancillary Reagent (pH 8.0) | | Visualization Reagent (pH 8.0) | |
|---|---|---|---|---|---|
| Component | Conc. | Component | Conc. | Component | Conc. |
| Tricine | 18.0 g/L | EPPS | 25.3 g/L | EPPS | 25.3 g/L |
| Sodium | 15.0 g/L | Sodium | 15.0 g/L | Sodium | 15.0 g/L |

TABLE 8-continued

Zika Ab assay formulation with goat-anti-human IgG Fc

| Chloride | | Chloride | | Chloride | |
|---|---|---|---|---|---|
| Tween 20 | 2.20 g/L | Tween 20 | 2.20 g/L | Tween 20 | 2.20 g/L |
| Disodium EDTA | 0.7 g/L | Disodium EDTA | 0.70 g/L | Disodium EDTA | 0.70 g/L |
| MICROPROTECT™ preservative | 2.50 mL/L | MICROPROTECT™ preservative | 1.0 mL/L | MICROPROTECT™ preservative | 1.0 mL/L |
| Sodium Azide | 0.9 g/L | Sodium Azide | 0.9 g/L | Sodium Azide | 0.9 g/L |
| BSA, Sulfhydryl Modified | 10.0 g/L | BSA, Sulfhydryl Modified | 10.0 g/L | BSA, Sulfhydryl Modified | 10.0 g/L |
| Heat Inactivated Goat Serum | 50.0 mL/L | Heat Inactivated Goat Serum | 400 mL/L | | |
| Goat Anti-Human IgG FC | 1.35 g/L | | | | |

Raw Materials

| Component | Conc. |
|---|---|
| Zika M Visualization Buffer (Zika NS1: NSP-DMAE-NHS) | 0.40 mg/L |
| SERA-MAG ® Magnetic Streptavidin Microparticles | 0.1 mg/mL |
| Biotinylated anti-human IgM monoclonal antibody | 0.04 mg/mg |

TABLE 9

Zika M assay formulation without goat-anti-human IgG Fc

| Buffer (pH 8.0) | | Ancillary Reagent (pH 8.0) | | Visualization Reagent (pH 8.0) | |
|---|---|---|---|---|---|
| Component | Conc. | Component | Conc. | Component | Conc. |
| Tricine | 18.0 g/L | EPPS | 25.3 g/L | EPPS | 25.3 g/L |
| Sodium Chloride | 15.0 g/L | Sodium Chloride | 15.0 g/L | Sodium Chloride | 15.0 g/L |
| Tween 20 | 2.20 g/L | Tween 20 | 2.20 g/L | Tween 20 | 2.20 g/L |
| Disodium EDTA | 0.7 g/L | Disodium EDTA | 0.70 g/L | Disodium EDTA | 0.70 g/L |
| Pluronic P-105 | 5.0 g/L | Pluronic P-105 | 5.0 g/L | Pluronic P-105 | 5.0 g/L |
| MICROPROTECT™ preservative | 2.50 mL/L | MICROPROTECT™ preservative | 1.0 mL/L | MICROPROTECT™ preservative | 1.0 mL/L |
| Sodium Azide | 0.9 g/L | Sodium Azide | 0.9 g/L | Sodium Azide | 0.9 g/L |
| BSA, Sulfhydryl Modified | 10.0 g/L | BSA, Sulfhydryl Modified | 10.0 g/L | BSA, Sulfhydryl Modified | 10.0 g/L |
| Heat Inactivated Goat Serum | 50.0 mL/L | Heat Inactivated Goat Serum | 400 mL/L | | |

Raw Materials

| Component | Conc. |
|---|---|
| Zika M Visualization Buffer (Zika NS1: NSP-DMAE-NHS) | 0.40 mg/L |
| SERA-MAG ® Magnetic Streptavidin Microparticles | 0.1 mg/mL |
| Biotinylated anti-human IgM monoclonal antibody | 0.04 mg/mg |

Results

Omitting goat-anti-human IgG Fc from the solid support buffer resolved the IgG detection issue, which was demonstrated through IgM blocking experiments (Table 10) and Zika IgG humanized monoclonal antibody dilution study (Table 11).

IgM Blocking Study

The blocking experiments (Table 10) were performed by pre-treating wetcake (SERA-MAG Magnetic Streptavidin Microparticles (MG-SA) (GE HealthCare Bio-Sciences Corp.) coated with anti-human IgM antibody) with non-specific human IgM (I8260, Sigma). Samples from Zika-positive several bleed panels were tested with the two formulations, one formulation with goat-anti-human IgG Fc (see Table 8) and another formulation without goat-anti-human IgG Fc (see Table 9) in which the wetcake had or had not been incubated with IgM blocker. Reactivity was analyzed by measuring relative light units (RLUs) and, the percent inhibition was calculated in the following manner:

$$\% \text{ Inhibition} = \frac{[(\text{No } IgM \text{ Blocking} - \text{Background}) - (\text{With } IgM \text{ Blocking} - \text{Background})]}{(\text{No } IgM \text{ Blocking} - \text{Background})}$$

Using the formulation with goat-anti-human IgG Fc, incubation with non-specific human IgM led to an average inhibition of only 39%. Using the formulation without goat-anti-human IgG Fc, incubation with non-specific human IgM resulted in 103% inhibition. This demonstrated that, in samples suspected to have Zika IgG, reactivity could be completely eliminated in the no goat-anti-human IgG Fc formulation (Table 10) by blocking with human IgM. Thus, the assay formulation without goat-anti-human IgG Fc does not bind human anti-Zika IgG.

TABLE 10

IgM Blocking: Compare formulation having goat-anti-human IgG Fc to formulation having no goat-anti-human IgG Fc

| Sample | Sample ID | Formulation with Goat Fc (Zika Ab) | | | Formulation No Goat Fc (Zika M) | | |
|---|---|---|---|---|---|---|---|
| | | No IgM Blocking | With IgM Blocking | Inhibition | No IgM Blocking | With IgM Blocking | Inhibition |
| Normal Donor | 2437115 | 13,767 | 14,360 | N/A | 12,843 | 19,639 | N/A |
| | 2437117 | 13,357 | 14,023 | N/A | 15,222 | 21,813 | N/A |
| | 2439148 | 13,142 | 14,471 | N/A | 10,806 | 19,493 | N/A |
| | 2439153 | 11,625 | 14,950 | N/A | 13,146 | 23,991 | N/A |
| Average Background | | 12,973 | 14,451 | N/A | 13,004 | 21,234 | N/A |
| Zika Positive Serial Draws | SD TDS0116V2 | 202,052 | 135,059 | 36% | N/A | N/A | N/A |
| | SD TDS0116V8 | 512,102 | 319,638 | 39% | N/A | N/A | N/A |
| | S-TDS0067V1 | 102,777 | 76,821 | 31% | N/A | N/A | N/A |
| | S-TDS0067V8 | 579,790 | 384,744 | 35% | N/A | N/A | N/A |
| | S-TDS0123V1 | 110,617 | 79,051 | 34% | 23,639 | 19,361 | 118% |
| | S-TDS0123V8 | 1,926,160 | 1,257,580 | 35% | 68,364 | 22,422 | 98% |
| | SD TDS0143V2 | 1,306,188 | 833,212 | 37% | 126,956 | 22,986 | 98% |
| | SD TDS0143V8 | 923,575 | 618,585 | 34% | 30,083 | 24,555 | 81% |
| | S-TDS0150V2 | 52,752 | 37,819 | 41% | 66,876 | 18,124 | 106% |
| | S-TDS0150V8 | 791,043 | 494,667 | 38% | 97,975 | 20,642 | 101% |
| | S-TDS0156V1 | 79,066 | 57,542 | 35% | 29,499 | 19,103 | 113% |
| | S-TDS0156V8 | 548,211 | 339,358 | 39% | 39,531 | 21,001 | 101% |
| | S-TDS0171V1 | N/A | N/A | N/A | 37,815 | 20,504 | 103% |
| | S-TDS0171V2 | 1,862,393 | 1,147,510 | 39% | N/A | N/A | N/A |
| | SD TDS0171V8 | 725,385 | 389,415 | 47% | 118,221 | 23,580 | 98% |
| | S-TDS0220V1 | 332,984 | 212,381 | 38% | 39,967 | 20,799 | 102% |
| | S-TDS0220V8 | 550,814 | 368,590 | 34% | 32,397 | 22,852 | 92% |
| | S-TDS0246V1 | 104,627 | 74,876 | 34% | 74,422 | 23,043 | 97% |
| | S-TDS0246V8 | 568,712 | 351,616 | 39% | 123,372 | 25,502 | 96% |
| | S-TDS0257V2 | 227,322 | 135,499 | 44% | 387,771 | 26,883 | 98% |
| | S-TDS0257V8 | 298,172 | 201,619 | 34% | 51,558 | 15,038 | 116% |
| | S-TDS0270V1 | 29,598 | 21,317 | 59% | 133,410 | 21,266 | 100% |
| | S-TDS0270V2 | 509,633 | 296,302 | 43% | 216,768 | 25,458 | 98% |
| | S-TDS0270V8 | 246,886 | 160,573 | 38% | N/A | N/A | N/A |
| | S-TDS0271V1 | 41,728 | 32,103 | 39% | 19,625 | 18,204 | 146% |
| | S-TDS0271V8 | 562,101 | 368,303 | 36% | 25,690 | 18,868 | 119% |
| | S-TDS0282V2 | 290,474 | 134,788 | 57% | 523,732 | 35,679 | 97% |
| | S-TDS0282V8 | 150,834 | 101,864 | 37% | 49,105 | 18,758 | 107% |
| | S-TDS0284V2 | 324,150 | 49,351 | 89% | 1,850,327 | 75,090 | 97% |
| | S-TDS0284V8 | 82,944 | 55,043 | 42% | 159,110 | 23,832 | 98% |
| | S-TDS0288V2 | 343,600 | 233,380 | 34% | 71,657 | 24,542 | 94% |
| | S-TDS0288V8 | 188,297 | 141,843 | 27% | 24,637 | 19,485 | 115% |
| | S-TDS0289V1 | 195,875 | 127,818 | 38% | 23,389 | 19,912 | 113% |
| | S-TDS0289V8 | 860,416 | 535,146 | 39% | 27,448 | 21,552 | 98% |
| | S-TDS0310V2 | 2,952,971 | 1,954,619 | 34% | 155,367 | 28,164 | 95% |
| | S-TDS0310V8 | 1,039,104 | 650,438 | 38% | 50,448 | 21,629 | 99% |
| | S-TDS0314V1 | 509,816 | 323,250 | 38% | 60,409 | 19,429 | 104% |
| | S-TDS0314V8 | 896,907 | 563,005 | 38% | 65,282 | 21,897 | 99% |
| | S-TDS0315V2 | 733,792 | 445,873 | 40% | 33,626 | 21,826 | 97% |
| | S-TDS0315V8 | 332,319 | 209,223 | 39% | 22,858 | 18,108 | 132% |
| | S-TDS0322V2 | 1,111,591 | 727,669 | 35% | 67,715 | 20,621 | 101% |
| | S-TDS0322V8 | 630,740 | 407,999 | 36% | 58,654 | 25,406 | 91% |

TABLE 10-continued

IgM Blocking: Compare formulation having goat-anti-human
IgG Fc to formulation having no goat-anti-human IgG Fc

| Sample | Sample ID | Formulation with Goat Fc (Zika Ab) | | | Formulation No Goat Fc (Zika M) | | |
|---|---|---|---|---|---|---|---|
| | | No IgM Blocking | With IgM Blocking | Inhibition | No IgM Blocking | With IgM Blocking | Inhibition |
| | S-TDS0345V2 | 99,900 | 57,264 | 51% | N/A | N/A | N/A |
| | S-TDS0345V8 | 141,480 | 94,846 | 37% | N/A | N/A | N/A |
| | S-TDS0362V2 | 195,550 | 114,925 | 45% | 202,942 | 28,319 | 96% |
| | S-TDS0362V8 | 251,220 | 157,971 | 40% | 33,200 | 20,973 | 101% |
| | S-TDS0396V1 | 114,005 | 78,597 | 37% | N/A | N/A | N/A |
| | S-TDS0396V2 | 1,451,870 | 975,558 | 33% | 95,521 | 21,929 | 99% |
| | S-TDS0396V8 | 634,572 | 386,259 | 40% | 38,965 | 18,728 | 110% |
| | S-TDS0401V2 | 906,881 | 569,003 | 38% | 27,095 | 19,024 | 116% |
| | S-TDS0401V8 | 297,200 | 187,950 | 39% | 27,929 | 18,227 | 120% |
| | S-TDS0422V1 | 369,715 | 226,977 | 40% | 136,705 | 24,481 | 97% |
| | S-TDS0422V8 | 222,534 | 141,486 | 39% | 62,710 | 20,654 | 101% |
| | S-TDS0468V1 | 158,078 | 113,324 | 32% | 69,662 | 22,190 | 98% |
| | S-TDS0468V2 | 554,736 | 359,027 | 36% | 225,839 | 23,850 | 99% |
| | S-TDS0468V8 | 729,933 | 473,088 | 36% | 98,505 | 21,813 | 99% |
| | S-TDS0478V2 | 475,450 | 293,242 | 40% | 103,273 | 21,893 | 99% |
| | S-TDS0478V8 | 435,118 | 278,252 | 38% | 21,930 | 20,127 | 112% |
| | S-TDS0499V2 | 1,254,676 | 821,953 | 35% | 64,277 | 21,236 | 100% |
| | S-TDS0499V8 | 912,477 | 582,515 | 37% | 30,958 | 20,927 | 102% |

Zika IgG Humanized Monoclonal Antibody Dilution Study

The cross-reactivity of Zika Ab assay (with goat anti-human Fc) and the Zika M assay (without goat anti-human Fc) to Zika-specific IgG was further evaluated using a monoclonal antibody IgG specific to Zika NS1. The monoclonal antibody (ZKA35) was obtained from HUMABS BioMed. Serial dilutions (0.001 ug/ml to 1.0 ug/ml) of ZKA35 were tested with the Zika Ab assay and the Zika M assay, as well as a prototype Zika Total assay (which was designed to detect both anti-Zika virus IgM and IgG antibodies).

The reactivity of each ZKA35 IgG dilutions with the respective Zika virus assays was calculated as signal (RLU)/cut-off (S/Co). Based on reactivity of samples from normal population and Zika PCR positive individuals, cut-offs of 42500, 70000 and 35000 were used for the Zika M assay, the Zika Ab assay, and the Zika Total assay, respectively. The S/Co of ≥1.0 was considered reactive with ZKA35 IgG.

The Zika Total assay, which detects both Zika IgG and IgM antibodies, was reactive with dilutions containing 0.063 µg/mL to 1.0 µg/mL of ZKA35 IgG (Table 11). The Zika Ab assay was reactive with dilutions containing 0.125 µg/mL to 1.0 µg/mL of ZKA35 IgG and showed approximately 10-fold lower reactivity compared to Zika Total assay at the highest ZKA35 IgG concentration. For the Zika M assay, all tested ZKA35 IgG dilutions were nonreactive (Table 11). These results demonstrate that while some Zika IgG cross-reactivity is seen with the Zika Ab assay, the Zika M assay does not cross-react with Zika specific IgG up to concentration of 1 µg/mL.

TABLE 11

Results from Zika IgG (ZKA35) Serial Dilution Study

| Zika IgG (ZKA35) Concentration (µg/mL) | Sample ID | Zika M | | Zika Ab | | Zika Total | |
|---|---|---|---|---|---|---|---|
| | | RLU | S/Co | RLU | S/Co | RLU | S/Co |
| 1.000 | MS012017A | 15,600 | 0.37 | 508,892 | 7.27 | 2,752,938 | 78.66 |
| 0.500 | MS012017B | 13,976 | 0.33 | 265,539 | 3.79 | 1,034,048 | 29.54 |
| 0.250 | MS012017C | 14,142 | 0.33 | 144,352 | 2.06 | 351,344 | 10.04 |
| 0.125 | MS012017D | 13,683 | 0.32 | 81,223 | 1.16 | 134,427 | 3.84 |
| 0.063 | MS012017E | 14,590 | 0.34 | 48,646 | 0.69 | 59,543 | 1.70 |
| 0.031 | MS012017F | 14,258 | 0.34 | 31,549 | 0.45 | 31,522 | 0.90 |
| 0.016 | MS012017G | 14,163 | 0.33 | 22,745 | 0.32 | 19,300 | 0.55 |
| 0.008 | MS012017H | 14,224 | 0.33 | 18,546 | 0.26 | 13,457 | 0.38 |
| 0.004 | MS012017I | 15,134 | 0.36 | 17,399 | 0.25 | 10,455 | 0.30 |
| 0.002 | MS012017J | 14,775 | 0.35 | 16,247 | 0.23 | 9,070 | 0.26 |
| 0.001 | MS012017K | 13,716 | 0.32 | 15,543 | 0.22 | 8,675 | 0.25 |

Standardization

The cutoff indices of the Zika Ab and Zika M assays were set based on testing presumed Zika virus negative normal donor samples (including pregnant women) from the US mainland, Zika virus PCR positive serial draws, and Dengue/West Nile virus positive cross-reactive samples (SeraCare Panel). The initial value of Zika Ab and Zika M standards was determined by testing the population mentioned above on a small lot of standards based on the cutoff during early development. Then a second larger lot of standards was built and values assigned from the previous small lots. These larger lots (Zika Ab Standards lot #16KL240 and Zika M standards lot #17CL059) served as the Anchor Standards for the standardization. Gold Standards are traceable to the Anchor Standards. Both Zika Ab and Zika M were assigned master curves and calibrator values were traceable to the internal gold standards. The Zika Ab and Zika M Gold Standards were used for evaluation and confirmation of reagent performance and in-process testing and value assignment of new lots of standards, calibrators, controls and medical decision pools.

The Zika Ab assay uses 6-level standards formulated with defibrinated and dialyzed human plasma. The Zika M assay also uses 6-level standards formulated with defibrinated and dialyzed human plasma. The Zika Ab and Zika M standards were built by spiking Zika IgM antibody positive pools into the Zika Ab and Zika M negative plasma pools respectively. The Zika Ab and Zika M standard levels S02-S06 are spiked with Zika M positive pools. The lowest Zika Ab and Zika M standard level S01 is unspiked Zika Ab and Zika M negative human plasma pools.

The Zika Ab and Zika M assays use 2 level calibrators formulated with defibrinated and dialyzed human plasma. The Zika Ab and Zika M high calibrator (above cutoff) was prepared by spiking Zika IgM antibody positive pools into the Zika Ab and Zika M negative plasma pools respectively. The Zika Ab and Zika M low calibrators (below cutoff) are unspiked Zika Ab and Zika M negative human plasma pools.

The Zika Ab and Zika M assays of the Zika Test use a 2-point calibration curve fit based on a 4PL-weighted curve fitting algorithm.

The Zika Ab and Zika M assays both use 2-level controls formulated with defibrinated, dialyzed human plasma. The Zika Ab and Zika M positive controls were prepared by spiking Zika IgM antibody positive pools into the Zika Ab and Zika gM negative plasma pools respectively. Both the Zika Ab and Zika IgM negative controls were unspiked Zika Ab and Zika M negative human plasma pools.

The Zika Ab and Zika M assays each have one level of Medical Decision Pools (MDPs) formulated with defibrinated and dialyzed human plasma. The Zika Ab and Zika M medical decision pools were prepared by spiking Zika M antibody positive pools into the Zika Ab and Zika M negative plasma pools respectively.

Those skilled in the art will appreciate that numerous changes and modifications can be made to the preferred and exemplified embodiments of the invention and that such changes and modifications can be made without departing from the spirit of the invention. It is, therefore, intended that the appended claims cover all such equivalent variations as fall within the true spirit and scope of the invention.

What is claimed is:

1. A method of detecting an anti-Zika virus IgM antibody in a biological sample from a human subject, the method comprising a first immunoassay and a second immunoassay, wherein the first immunoassay comprises:

a) incubating a first biological sample from the human subject with a labeled Zika virus antigen and
a buffer comprising an anti-human IgG Fc antibody and
a solid support comprising an anti-human IgM antibody,
a labeled Zika virus antigen,
wherein, in the presence of an anti-Zika virus IgG antibody, an anti-Zika virus IgM antibody, or an anti-Zika virus IgG antibody and an anti-Zika virus IgM antibody in the biological sample, a complex I is formed, the complex I comprising (i) the anti-Zika virus IgG antibody, the anti-Zika virus IgM antibody, or the anti-Zika virus IgG antibody and the anti-Zika virus IgM antibody, (ii) the labeled Zika virus antigen, and (iii) the solid support comprising the anti-human IgM antibody; and b) detecting the presence of complex I, the presence of which indicates the presence of the anti-Zika virus IgM antibody, the anti-Zika virus IgG antibody, or the anti-Zika virus IgG antibody and the anti-Zika virus IgM antibody in the biological sample, and wherein the second immunoassay comprises incubating a second biological sample from the human subject with a labeled Zika virus antigen and a solid support comprising an anti-human IgM antibody, wherein anti-human IgG Fc antibody is absent from the second immunoassay, and wherein, in the presence of an anti-Zika virus IgM antibody in the second biological sample, a complex II is formed, the complex II comprising (i) the solid support comprising the anti-human IgM antibody, (ii) the anti-Zika virus IgM antibody, and (iii) the labeled Zika virus antigen; and d) detecting the presence or absence of complex II, the presence of which indicates the presence of the anti-Zika virus IgM antibody in the second biological sample.

2. The method of claim 1, wherein the label comprises an enzyme conjugate, a fluorescent probe, a radioactive isotope, a chemiluminescent compound, a bioluminescent compound, or a combination thereof.

3. The method of claim 2, wherein the label comprises an acridinium ester (AE) or an analog thereof.

4. The method of claim 3, wherein the AE or analog thereof is dimethyl acridinium ester (DMAE), N-sulfopropyl dimethyl acridinium ester (NSP-DMAE), high quantum yield acridinium ester (HQYAE, acridinium, 9-[[4-[[[6-[(2,5-dioxo-1-pyrrolidinyl)oxyl-6-oxohexyllaminolcarbonyl1-2,6-dimethylphenoxy]carbonyl]-2,7-bis(3,6,9,12,15,18-hexaoxanonadec-1-yloxy)-10-(3-sulfopropyl)-, inner salt), Zwitterionic acridinium ester (ZAE, Acridinium, 9-[[4-[[[3-[[3-[[5-[(2,5-dioxo-1-pyrrolidinyl)oxy]-1,5 -dioxopentylja-minojpropyljmethyl(3-sulfopropyl)ammoniojpropyljami-nojcarbonyl]-2,6-dimethylphenoxyjcarbonylj-10-(3-sulfopropyl)-, bis(inner salt)), N-sulfopropyl-2-isopropoxy dimethyl acridinium ester (Iso-Di-ZAE), trisulfopropyl acridinium ester (TSP-AE), or N-sulfopropyl dimethyl acridinium ester with hexa(ethylene)glycol linker (HEG-GLU-AE).

5. The method of claim 1, wherein the Zika virus antigen is Zika virus NS1 antigen, or an immunogenic fragment thereof.

6. The method of claim 5, wherein the Zika virus NS1 antigen or immunogenic fragment thereof is recombinant.

7. The method of claim 1, wherein the anti-human IgG Fc antibody is a monoclonal or a polyclonal antibody.

8. The method of claim 1, wherein the anti-human IgG Fc antibody is a goat-anti-human IgG Fc antibody.

9. The method of claim 1, wherein the anti-human IgM antibody is indirectly linked to the solid support.

10. The method of claim 9, wherein the anti-human IgM antibody is biotinylated and the solid support comprises streptavidin.

11. The method of claim 1, wherein the anti-human IgG Fc antibody is indirectly linked to the solid support.

12. The method of claim 11, wherein the anti-human IgG Fc antibody is biotinylated and the solid support comprises streptavidin.

13. The method of claim 1 wherein the first biological sample is serum or plasma and the second biological sample is serum or plasma.

14. The method of claim 13, wherein the first biological sample, the second biological sample, or both further comprises an anticoagulant.

15. The method of claim 14, wherein the anticoagulant comprises ethylenediaminetetraacetic acid (EDTA) or heparin.

16. The method of claim 1 wherein the first biological sample the second biological sample, or both are obtained from the subject at least 8 days after onset of symptoms of Zika virus infection or risk of exposure to Zika virus.

17. The method of claim 1, wherein, in the first immunoassay, the anti-human IgM antibody and the solid support are present in a buffer comprising tricine, sodium chloride, polyoxyethylene (20) sorbitan monolaurate, disodium ethylenediaminetetraacetic acid (EDTA), preservative, sulfhydryl-modified bovine serum albumin, and the anti-human IgG Fc antibody, and wherein, in the second immunoassay, the anti-human IgM antibody and the solid support are present in a buffer comprising tricine, sodium chloride, polyoxyethylene (20) sorbitan monolaurate, disodium EDTA, preservative, sulfhydryl-modified bovine serum albumin, but without the anti-human IgG Fc antibody.

18. The method of claim 1, wherein the solid support comprises a column matrix material, a culture plate, a tube, a dish, a flask, a microtiter plate, a bead, or a combination thereof.

19. The method of claim 1, wherein the solid support comprises a paramagnetic particle (PMP) or a latex magnetic particle (LMP).

20. The method of claim 1, wherein the Zika virus antigen comprises an epitope tag, wherein the epitope tag is a 6-histidine tag, a hemagglutinin tag, a glutathione-S-transferase, a maltose binding protein, or a chitin binding protein.

21. The method of claim 1, further comprising determining a level of the anti-Zika virus IgG antibody, the anti-Zika virus IgM antibody, or the anti-Zika virus IgG antibody and the anti-Zika virus IgM antibody in the biological sample.

22. The method of claim 21, wherein the level of the anti-Zika virus IgG antibody, the anti-Zika virus IgM antibody, or the anti-Zika virus IgG antibody and the anti-Zika virus IgM antibody in the biological sample is directly proportional to the level of the complex I or complex II detected.

23. The method of claim 1, wherein the detecting comprises measuring a signal from the label and comparing the signal to a control signal from a biological sample from a human known to be negative for anti-Zika virus antibodies.

24. The method of claim 1, wherein, if the complex II is detected, performing the second immunoassay further comprises repeating steps c) and d) at least in duplicate.

25. The method of claim 24, wherein the method further comprises determining that the human subject is positive for anti-Zika virus IgM antibodies if the complex II is detected in the equivalent of at least 2 of 3 replicates.

26. A method of detecting antibodies to Zika virus in a human subject, the method comprising performing a first immunoassay comprising:
a) incubating a first biological sample from the subject with:
a buffer comprising an anti-human IgG Fc antibody and a solid support comprising an anti-human IgM antibody,
a labeled Zika virus antigen,
wherein, in the presence of an anti-Zika virus IgG antibody, an anti-Zika virus IgM antibody, or an anti-Zika virus IgG antibody and an anti-Zika virus IgM antibody in the biological sample, a complex I is formed, the complex I comprising (i) the solid support comprising the anti-human IgM antibody, (ii) the anti-Zika virus IgG antibody, the anti-Zika virus IgM antibody, or the anti-Zika virus IgG antibody and the anti-Zika virus IgM antibody, and (iii) the labeled Zika virus antigen;
b) detecting the presence of complex I, and
performing a second immunoassay comprising:
c) incubating a second biological sample from the subject with:
a solid support comprising an anti-human IgM antibody, and
a labeled Zika virus antigen,
wherein anti-human IgG Fc antibody is absent from the second immunoassay,
wherein, in the presence of an anti-Zika virus IgM antibody in the second biological sample, a complex II is formed, the complex II comprising (i) the solid support comprising the anti-human IgM antibody, (ii) the anti-Zika virus IgM antibody, and (iii) the labeled Zika virus antigen;
d) detecting the presence or absence of complex II, and
di) if the complex II is not detected, determining that the human subject is negative for anti-Zika virus IgM antibodies, or
dii) if the complex II is detected, repeating steps c) and d) at least in duplicate, and
e) if the complex II is detected in the equivalent of at least 2 of 3 replicates, determining that the human subject is positive for anti-Zika virus IgM antibodies.

27. The method of claim 26, wherein the detecting comprises measuring a signal from the label and comparing the signal to a control signal from a biological sample from a human known to be negative for anti-Zika virus antibodies.

28. A kit comprising reagents for a first immunoassay and reagents for a second immunoassay,
wherein the reagents for the first immunoassay comprise:
a solid support comprising an anti-human IgM antibody in a buffer comprising comprising tricine, sodium chloride, polyoxyethylene (20) sorbitan monolaurate, disodium ethylenediaminetetraacetic acid (EDTA), preservative, sulfhydryl-modified bovine serum albumin, and an anti-human IgG Fc antibody, and
a labeled Zika virus antigen; and
wherein the reagents for the second immunoassay comprise:
a solid support comprising an anti-human IgM antibody, in a buffer comprising tricine, sodium chloride, polyoxyethylene (20) sorbitan monolaurate, disodium EDTA, preservative, sulfhydryl-modified bovine serum albumin, but without anti-human IgG Fc antibody, and
a labeled Zika virus antigen.

29. The kit of claim 28, further comprising instructions for performing the first and the second immunoassays, wherein the instructions direct a user to perform the first immunoassay to determine the presence or absence of anti-Zika Virus antibodies in a biological sample from a human subject, and wherein the instructions further direct the user to perform the second immunoassay only if it is determined in the first immunoassay that the biological sample is positive for anti-Zika Virus antibodies.

30. The kit of claim 28, wherein the label comprises an enzyme conjugate, a fluorescent probe, a radioactive isotope, a chemiluminescent compound, a bioluminescent compound, or a combination thereof.

31. The kit of claim 29, wherein the label is an acridinium ester (AE) or an analog thereof.

32. The kit of claim 28, wherein the solid support comprises a column matrix material, a culture plate, a tube, a dish, a flask, a microtiter plate, a bead, a microparticle, or a combination thereof.

33. The kit of claim 32, wherein the solid support is a paramagnetic particle (PMP) or a latex magnetic particle (LMP).

* * * * *